United States Patent [19]

Kato

[11] Patent Number: 4,543,479
[45] Date of Patent: Sep. 24, 1985

[54] RADIATION IMAGE RECORDING AND READ-OUT SYSTEM

[75] Inventor: Hisatoyo Kato, Kaisei, Japan

[73] Assignee: Fuji Photo Film Co. Ltd., Kanagawa, Japan

[21] Appl. No.: 434,883

[22] Filed: Oct. 18, 1982

[30] Foreign Application Priority Data

Oct. 16, 1981 [JP] Japan ................. 56-165118
Oct. 16, 1981 [JP] Japan ................. 56-165122
Oct. 16, 1981 [JP] Japan ................. 56-165123
May 19, 1982 [JP] Japan ................. 57-84436

[51] Int. Cl.$^4$ ............................................. G01T 1/105
[52] U.S. Cl. ................................................ 250/327.2
[58] Field of Search ............... 250/327.2, 337, 484.1

[56] References Cited

U.S. PATENT DOCUMENTS

| | | | |
|---|---|---|---|
| 2,482,813 | 9/1949 | Urbach | 430/139 |
| 3,246,148 | 4/1966 | Detroeyer et al. | 430/126 |
| 4,258,264 | 3/1981 | Kotera et al. | 250/484.1 |
| 4,276,473 | 6/1981 | Kato et al. | 250/327.2 |
| 4,302,672 | 11/1981 | Kato et al. | 250/327.2 |
| 4,310,886 | 1/1982 | Kato et al. | 364/414 |
| 4,315,318 | 2/1982 | Kato et al. | 382/6 |
| 4,346,295 | 8/1982 | Tanaka et al. | 250/327.2 |
| 4,369,367 | 1/1983 | Horikawa | 250/327.2 |
| 4,387,428 | 6/1983 | Ishida et al. | 364/414 |
| 4,394,581 | 7/1983 | Takahashi et al. | 250/484.1 |
| 4,400,619 | 8/1983 | Kotera et al. | 250/327.2 |
| 4,439,866 | 3/1984 | Kato et al. | 378/19 |

Primary Examiner—Janice A. Howell
Assistant Examiner—Constantine Hannaher
Attorney, Agent, or Firm—Murray, Whisenhunt & Ferguson

[57] ABSTRACT

In a radiation image recording system in which a radiation image is once recorded on a stimulable phosphor and then read out to reproduce a visible radiation image, at least one recording material formed of a phosphor layer and fixed on a supporting material is circulated and reused to record radiation images thereon. The system comprises a mechanism for circulating the recording material with respect to the image read-out section by repeatedly moving the supporting material and the image read-out section with respect to each other, and an erasing apparatus for eliminating the radiation energy remaining on the recording material after the read-out step. The supporting material is an endless belt, a rotatable drum or a plate, and the recording material is a continuous phosphor layer or a phosphor sheet.

10 Claims, 11 Drawing Figures

RADIATION IMAGE RECORDING AND READ-OUT SYSTEM

BACKGROUND OF THE INVENTION

1. Field of the Invention

This invention relates to a radiation image recording and read-out system for exposing a stimulable phosphor to a radiation to have a radiation image stored therein, scanning the stimulable phosphor with a stimulating ray to cause the stimulable phosphor carrying the radiation image to emit light in the pattern of the radiation image stored therein, reading out the emitted light to obtain an electric signal, and reproducing a visible image by use of the obtained electric signal. More particularly, this invention relates to a radiation image recording and read-out system in which the stimulable phosphor is circulated and reused to record radiation images.

2. Description of the Prior Art

When certain kinds of phosphors are exposed to a radiation such as X-rays, $\alpha$-rays, $\beta$-rays, $\gamma$-rays or ultraviolet rays, they store a part of the energy of the radiation. Then, when the phosphor which has been exposed to the radiation is exposed to a stimulating ray such as visible light, light is emitted from the phosphor in proportion to the stored energy of the radiation. A phosphor exhibiting such properties is referred to as a stimulable phosphor.

As disclosed in U.S. Pat. Nos. 4,258,264, 4,276,473 and 4,315,318, U.S. patent application Ser. No. 220,780, U.S. Pat. No. 4,387,428, Japanese Unexamined Patent Publication No. 56(1981)-11395, it has been proposed to use the stimulable phosphor for recording a radiation image of the human body for medical diagnosis. Specifically, the stimulable phosphor is first exposed to a radiation to have a radiation image stored therein, and is then scanned with a stimulating ray which causes it to emit light in the pattern of the stored image. The light emitted from the stimulable phosphor upon stimulation thereof is photoelectrically detected and converted to an electric image signal, which is processed as desired to reproduce a visible image of a quality suitable for viewing and diagnostic purposes. The final visible image may be reproduced in the form of a hard copy or may be displayed on a cathode ray tube (CRT). The stimulable phosphor sheet used in this method may be in any of various forms such as a panel, drum or the like, which are herein generally referred to as sheets. In this radiation image recording and reproducing method, the stimulable phosphor sheet is used to temporarily store the radiation image in order to reproduce the final visible image therefrom on a final recording medium. For economical reasons, therefore, it is desirable that the stimulable phosphor sheet be used repeatedly.

In order to reuse the stimulable phosphor sheet, the radiation energy remaining on the stimulable phosphor sheet after it is scanned with a stimulating ray to read out the radiation image stored thereon should be eliminated or erased by the method described, for example, in Japanese Unexamined Patent Publication No. 56(1981)-11392 or 56(1981)-12599. Practically, it is possible to save manpower by supplying the stimulable phosphor sheet to an image erasing apparatus by use of a conveying means such as a belt conveyor after the radiation image is read out from the stimulable phosphor sheet, and returning the stimulable phosphor sheet to the image recording section by use of a similar conveying means after the radiation image remaining on the stimulable phosphor sheet is erased.

In general, however, it is not easy to design and manufacture a conveying means which can convey a sheet material like the stimulable phosphor sheet without any failure due to clogging, sheets caught at an intermediate point, or the like. Further, the stimulable phosphor sheet must be conveyed in the intact form without being scratched or flawed. This also makes it difficult to design and manufacture the conveying means. Furthermore, it sometimes happens that some phosphor sheets are processed for reproducing the radiation images therefrom immediately after the radiation images are recorded thereon, and some are processed later together with the others. As a result, the sequence of using the phosphor sheets is disordered, and the new and old phosphor sheets are sent in the mixed form to the image recording section. In this case, it is impossible to obtain reproduced images of a uniform quality since the quality of the reproduced images differs between the new and old phosphor sheets. Thus, it is desired to replace the old phosphor sheets with new ones when necessary. For this purpose, it is necessary to inspect the quality of images reproduced from the respective phosphor sheets or to control the number of repetitions of the recording operations for the respective phosphor sheets, thereby to determine whether to replace the phosphor sheets with new ones or to reuse them for further recording operations. However, it is very troublesome to conduct quality control for individual phosphor sheets.

Further, in a movable X-ray diagnostic station such as a traveling X-ray diagnostic station in the form of a vehicle like a bus which is provided with the radiation image recording and read-out system and travels for recording radiation images for the purpose of collective medical examination, the amount of the recording materials capable of being loaded on the movable radiographic station is limited. Therefore, it is desired to load the stimulable phosphor sheets which can be used repeatedly on the movable radiographic station, once store the radiation images of the objects on the phosphor sheets, transfer the electric image signals read out from the phosphor sheets into a recording medium having a large storage capacity, such as a magnetic tape, circulate and reuse the phosphor sheets for further recording and read-out operations, thereby to obtain the radiation image signals of many objects. In this case, it is not necessary to load a number of stimulable phosphor sheets or panels having a relatively large size (for example, having a size of a conventional X-ray film cassette).

Particularly, when the elements of the system, e.g. the circulatable and reusable recording materials formed of a stimulable phosphor, the image recording section for exposing each recording material to a radiation passing through the object, the image read-out section for reading out the radiation image stored in the recording material, and the erasing means for erasing the radiation energy remaining on the recording material after the read-out step to again record another radiation image thereon, are combined into one unit, the system can easily be loaded on the movable radiographic station for traveling to conduct medical examination and can also be easily installed in a hospital or the like. This is very advantageous in practical use.

SUMMARY OF THE INVENTION

The primary object of the present invention is to provide a radiation image recording and read-out system in which the stimulable phosphor for recording a radiation image therein can be circulated and reused to repeatedly form reproduced visible images having a uniform quality.

Another object of the present invention is to provide a radiation image recording and read-out system which is easy to design, manufacture, control and move.

The specific object of the present invention is to provide a radiation image recording and read-out system which is small in size, light in weight, and suitable for installation in a movable radiographic station, a hospital, or the like.

The radiation image recording and read-out system in accordance with the present invention comprises at least one recording material comprised of a stimulable phosphor layer and fixed on a supporting material, an image recording section for exposing said recording material to a radiation passing through an object to have a radiation transmission image of the object stored on said recording material, an image read-out section provided with a photoelectric read-out means for scanning said recording material with a stimulating ray which causes it to emit light and reading out the emitted light to obtain an electric image signal, a means for moving said recording material with respect to said recording section and said image read-out section, and an erasing means for eliminating the radiation energy remaining on said recording material after the read-out step.

In the present invention, the electric image signal obtained in the image read-out section may then be once stored on a recording medium such as a magnetic tape or a magnetic disk, displayed on a CRT or the like to immediately observe the radiation image, or permanently recorded as a hard copy on a photographic material or the like by use of a reproducing apparatus. The reproducing apparatus may be directly coupled with the system in accordance with the present invention, installed separately from the system for conducting reproduction via a memory, or placed at a remote position for conduction reproduction through radio communication. In the case mentioned last, it is possible, for example, to reproduce the radiation image recorded in the movable X-ray diagnostic station by use of a radio signal receiver in a hospital, and informing the results of diagnosis conducted by the radiologist to the movable X-ray diagnostic station through radio communication.

In the radiation image recording and read-out system in accordance with the present invention, the recording materials formed of stimulable phosphor layers for recording radiation images therein are circulated and reused in the form fixed on a supporting material. Since the recording materials are circulated and reused in good order unlike the phosphor sheets which are used in the discrete form, it is possible to always obtain reproduced images of a uniform, stable quality without any risk of the recording materials damaged. Further, the system is easy to conduct quality control since, when the stimulable phosphor layers are deteriorated, all layers can be replaced by new ones. Since the recording materials are built in the system, it is easy to handle them and to operate the system. Furthermore, since the system has a simple construction, it is easy to design and manufacture, small in size and light in weight. Accordingly, the system in accordance with the present invention is very suitable for installation in a movable radiographic station, a hospital, or the like. This is very advantageous in practical use.

The stimulable phosphor referred to in this invention means a phosphor which is able to store radiation energy upon exposure thereof to such radiation as X-rays, $\alpha$-rays, $\beta$-rays, $\gamma$-rays or ultraviolet rays, and then emits light in proportion to the stored energy of the radiation upon stimulation with a stimulating ray such as a visible ray.

In the present invention, in order to improve the signal-to-noise ratio of the image signal obtained, it is desirable to make the wavelength distribution of the stimulating ray different from and far apart from the wavelength distribution of the light emitted from the stimulable phosphor. Therefore, it is preferable that the stimulating ray and the stimulable phosphor be selected to satisfy this requirement. Preferably, the stimulable phosphor should emit light having a wavelength within the range between 300 nm and 500 nm, and the wavelength of the stimulating ray should be within the range between 450 nm and 700 nm.

As the stimulable phosphor capable of emitting light having a wavelength within the range between 300 nm and 500 nm, for example, rare earth element activated alkaline earth metal fluorohalide phosphor is preferred. One example of this phosphor is, as shown in Japanese Unexamined Patent Publication No. 55(1980)-12143, a phosphor represented by the formula $(Ba_{1-x-y},Mg_x,Ca_y)FX:aEu^{2+}$ wherein X is at least one of Cl and Br, x and y are numbers satisfying $0 < x+y \leq 0.6$ and $xy \neq 0$, and a is a number satisfying $10^{-6} \leq a \leq 5 \times 10^{-2}$. Another example of this phosphor is, as shown in Japanese Unexamined Patent Publication No. 55(1980)-12145, a phosphor represented by the formula $(Ba_{1-x},M^{II}_x)FX:yA$ wherein $M^{II}$ is at least one of Mg, Ca, Sr, Zn and Cd, X is at least one of Cl, Br and I, A is at least one of Eu, Tb, Ce, Tm, Dy, Pr, Ho, Nd, Yb and Er, x is a number satisfying $0 \leq x \leq 0.6$, and y is a number satisfying $0 \leq y \leq 0.2$. Further, as the stimulable phosphor can be used ZnS:Cu,Pb; $BaQ.xAl_2O_3:Eu$ wherein $0.8 \leq x \leq 10$; and $M^{II}O.xSiO_2$: A wherein $M^{II}$ is Mg, Ca, Sr, Zn, Cd or Ba, A is Ce, Tb, Eu, Tm, Pb, Tl, Bi or Mn, and x is a number satisfying $0.5 \leq x \leq 2.5$, as shown in Japanese Unexamined patent Publication No. 55(1980)-12142. Furthermore, as the stimulable phosphor can be used LnOX:xA wherein Ln is at least one of La, Y, Gd and Lu, X is at least one of Cl and Br, A is at least one of Ce and Tb, x is a number satisfying $0 \leq x \leq 0.1$, as shown in Japanese Unexamined Patent Publication No. 55(1980)-12144. Among the above enumerated phosphors, the rare earth element activated alkaline earth metal fluorohalide phosphor is the most preferable, among which barium fluorohalides are the most preferable in view of the high intensity of emission of light.

Further, barium fluorohalide phosphors added with a metal fluoride as disclosed in Japanese Unexamined Patent Publication Nos. 56(1981)-2385 and 56(1981)-2386, or barium fluorohalide phosphors added with at least one of a metal chloride, a metal bromide and a metal iodide as disclosed in Japanese Patent Application No. 54(1979)-150873 are also preferable because of their improved light emitting characteristics.

It is also desirable to color the stimulable phosphor layer constituting the recording material made of the above phosphor by use of pigments or dyes to improve the sharpness of the image obtained thereby as disclosed in U.S. patent application Ser. No. 156,520, U.S. Pat. No. 4,394,581.

DESCRIPTION OF THE PREFERRED EMBODIMENTS

The present invention will hereinbelow be described in further detail with reference to the accompanying drawings.

Figure 1:
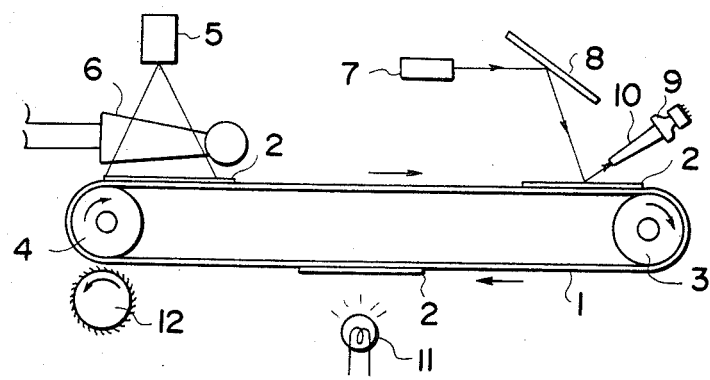
FIG. 1 is a schematic view showing the first embodiment of the radiation image recording and read-out system in accordance with the present invention.

In FIG. 1, an endless conveyor 1, e.g. a belt conveyor or a chain conveyor, is used as the supporting material for supporting the three stimulable phosphor sheets. These stimulable phosphor sheets 2 are fixed in equally spaced relation on the conveyor 1. The conveyor 1 provided with the phosphor sheets 2 is engaged with a driving roller 3 and a driven roller 4, and moved in the direction of the arrow by the driving roller 3 which is rotated by a drive unit (not shown). In the vicinity of the driven roller 4 is positioned a radiation source 5 to face the conveyor 1. The radiation source 5 may be an X-ray source or the like, and projects a radiation transmission image of an object 6 positioned between the phosphor sheet 2 and the radiation source 5 onto the phosphor sheet 2. In the vicinity of the driving roller 3 are positioned a stimulating ray source 7 for emitting a stimulating ray such as a laser beam, a light deflector 8 formed of a galvanometer mirror or the like for deflecting the stimulating ray emitted from the stimulating ray source 7 in the width direction of the conveyor 1, and a photodetector 9 for reading out the light emitted from the phosphor sheet 2 upon stimulation thereof by the stimulating ray. The photodetector 9 may be formed of a head-on type photomultiplier, a photoelectric amplification channel plate or the like. The photodetector 9 detects the light emitted from the phosphor sheets 2 upon stimulation thereof and guided by a light transfer means 10. An erasing light source 11 is positioned to face the conveyor 1 on the side opposite to the radiation source 5, the stimulating ray source 7 and the photodetector 9. The erasing light source 11 emits light having a wavelength within the stimulation wavelength range of the phosphor sheets 2 irradiated onto the phosphor sheets 2 to cause them to emit the radiation energy stored thereon. The erasing light source 11 may be formed, e.g., of a tungsten-filament lamp, halogen lamp, infrared lamp, or laser source as described in Japanese Unexamined Patent Publication No. 56(1981)-11392. Since the radiation energy stored on the phosphor sheets 2 can also be eliminated by heating them as disclosed, for example, in Japanese Unexamined Patent Publication No. 56(1981)-12599, the erasing light source 11 may be replaced by a heating means. A cylindrical cleaning roller 12 is opposed to the driven roller 4 with the conveyor 1 intervening therebetween. The cleaning roller 12 is rotated counterclockwise in the diagram by a drive unit (not shown), and removes dust from the surfaces of the phosphor sheets 2 moving in contact with the cleaning roller 12. If necessary, the cleaning roller 12 may be of an electrostatic attraction type which collects dust and the like by an electrostatic force.

The light transfer means 10 may be of a material and a construction as disclosed in U.S. Pat. No. 4,346,295, U.S. patent application Ser. No. 168,805, U.S. Pat. No. 4,369,367, Japanese Unexamined Patent Publication No. 56(1981)-11395, and may be used by the method disclosed therein.

The radiation image recording and read-out system shown in FIG. 1 is operated as described below. The conveyor 1 is intermittently moved the distance corresponding to one-third of the entire circumference thereof at a time by the driving roller 3. The stopping position of the conveyor 1 are set so that one phosphor sheet 2 faces the radiation source 5 when the conveyor 1 stops. When the conveyor 1 is stopped, the radiation source 5 is turned on to cause the phosphor sheet 2 facing the radiation source 5 to store the radiation transmission image of the object 6. After the radiation image is recorded on the phosphor sheet 2, the conveyor 1 is further moved the distance of one-third the conveyor circumference and stopped. At this time, the phosphor sheet 2 carrying the radiation image stored thereon is stopped in the position facing the light deflector 8 and the photodetector 9, and scanned with the stimulating ray emitted from the stimulating ray source 7. Scanning is conducted in the width direction of the conveyor 1 (main scanning) by the light deflector 8, and also in the length direction of the conveyor 1 (subsidiary scanning) by the movement of a stage (not shown) carrying the stimulating ray source 7, the light deflector 8, the photodetector 9 and the light transfer means 10 in the length direction of the conveyor 1. The stage can be easily formed by use of a known linear movement mechanism. Upon exposure to the stimulating ray, the phosphor sheet 2 emits light in the pattern of the radiation image stored thereon. The emitted light is inputted to the photodetector 9 via the light transfer means 10, and an electric signal corresponding to the radiation image stored on the phosphor sheet 2 is outputted from the photodetector 9. After the radiation image is read out in this way, the conveyor 1 is further moved the distance of one-third the circumference thereof and stopped. In this condition, the phosphor sheet 2 from which the radiation image has been read out is opposed to the erasing light source 11, and exposed to the erasing light emitted therefrom to eliminate the radiation energy of the radiation image remaining on the phosphor sheet 2 after the read-out step, the radiation emitted from radioactive isotopes such as $^{266}$Ra and $^{40}$K existing in trace amounts in the stimulable phosphor, and environmental radiations stored in the stimulable phosphor. In this way, the phosphor sheet 2 is recovered to the condition usable for recording a further radiation image. Thereafter, the conveyor 1 is moved the distance of one-third the conveyor circumference until the erased phosphor sheet 2 faces the radiation source 5. Midway during this movement, dust on the surface of the phosphor sheet 2 is removed by the cleaning roller 12. The phosphor sheet 2 free from any radiation energy and dust is reused to record a radiation image at the radiation source 5.

As described above, the stimulable phosphor sheets 2 are circulated and reused through the erasing step conducted by the erasing light source 11 and the cleaning step effected by the cleaning roller 12. One phosphor sheet 2 passes through the image recording, image read-out and image erasing steps while the conveyor 1 rotates one turn. It is, of course, possible to simultaneously conduct these three steps for the three phosphor sheets 2, respectively, when the conveyor 1 is stopped. In this case, it is possible to improve the image processing speed.

In the embodiment shown in FIG. 1, since the phosphor sheets 2 are fixed on the endless conveyor 1 and reused through the circulation of the conveyor 1, there is no risk of the stimulable phosphor being damaged unlike the method in which discrete phosphor sheets are conveyed one by one. Further, since the mechanism for circulating the phosphor sheets 2 can be formed of a simple conveyor mechanism, the system is easy to design and manufacture. Also, since the three phosphor sheets 2 are always used in the predetermined sequence, the quality of the reproduced images does not fluctuate among the phosphor sheets.

The electric image signal obtained from the photodetector 9 may immediately be sent to a reproducing apparatus to reproduce the radiation image as a hard copy or display it on a CRT, or may be digitized and temporarily stored on a high-density recording medium such as a magnetic tape, magnetic disk or optical disk to later reproduce the radiation image therefrom. When the system in accordance with the present invention is loaded on a traveling X-ray diagnostic station or the like for obtaining radiation images for medical diagnosis, it is possible to reduce the number of equipment to be loaded on the traveling station by conducting the read-out and storing of the electric image signals on the high-density recording medium at the site of recording and read-out operation, and bringing the recording medium to a medical center or the like for reproducing the radiation images. The electric image signals may also be simultaneously inputted to the reproducing apparatus and the recording medium. Namely, when the system is used in a hospital, the electric image signals may be transferred from the recording and read-out station to the recording medium for storage station where the image signals are temporarily stored in a recording midium and, at the same time, they may be transferred to the reproducing apparatus, e.g. a CRT, in the diagnostic room in order to immediately use them for diagnosis.

It is possible and preferable for obtaining a radiation image having a high diagnostic efficiency and accuracy to process the electric image signal in order to intensify the image and change the contrast. In the present invention, it is preferable to conduct the frequency processing as disclosed in U.S. Pat. No. 4,315,318, U.S. patent application Ser. Nos. 105,240, and 220,780, U.S. Pat. No. 4,346,295, Japanese Unexamined Patent Publication Nos. 56(1981)-75137, 56(1981)-75139 and 56(1981)-75141, and/or the gradation processing as disclosed in U.S. Pat. Nos. 4,302,672, 4,276,473 and 4,310,886.

In the embodiment shown in FIG. 1, the subsidiary scanning of the stimulable phosphor sheets 2 is conducted by moving the stimulating ray source and read-out apparatus with respect to the stationary phosphor sheets 2. However, it is also possible to maintain the stimulating ray source and read-out apparatus stationary, and move the phosphor sheets 2 to conduct the subsidiary scanning. In order to move the phosphor sheets 2 for this purpose, it is possible to mount the phosphor sheets 2 on the conveyor 1 via a stage, instead of directly fixing them thereon, move the stage on the conveyor 1 when the conveyor 1 is being halted to read out the radiation image, and return the stage to a predetermined position after the read-out is over. Alternatively, the phosphor sheets may be directly mounted on the conveyor 1, and the subsidiary scanning may be conducted by moving the conveyor 1. In the latter case, the distance between the image recording section and the image read-out section may be made different from the intervals between the adjacent phosphor sheets 2, and after the conveyor 1 has been moved to scan one phosphor sheet 2 in the subsidiary direction, the conveyor 1 may be moved to a position to locate the next phosphor sheet 2 at the image recording section. In this case, the image recording and the image read-out are not conducted at the same time. Further, in order to speed up the recording and read-out operation by carrying out the image recording and the image read-out in parallel with each other, it is possible to move the conveyor 1 to scan one phosphor sheet 2 in the subsidiary scanning direction while a radiation image is being recorded on the next phosphor sheet 2, which is being moved together with the conveyor 1, by use of the slit exposure method. It is also possible to use several conveyors that can automatically transfer the phosphor sheets 2 therebetween, and operate the conveyors in such a way that the phosphor sheets 2 are ultimately circulated via these conveyors. In this case, when the read-out speed is extremely lower than the recording speed, it becomes possible to increase the read-out speed by installing a plurality of image read-out sections for one image recording section, connecting the conveyors branched from the image recording section to the respective image read-out sections, and supplying the phosphor sheets 2 to the respective image read-out sections. Further, when the phosphor sheets 2 are transferred among a plurality of conveyors as described above, it is possible to connect two conveyors via one stage for temporarily storing the phosphor sheets 2. This connection method is convenient since deteriorated phosphor sheets can be removed from the system or new phosphor sheets can be added thereto by use of this stage without stopping the system.

In the first embodiment described above, since the stimulable phosphor sheets 2 are fixed on the conveyor 1 in engagement with the rollers 3 and 4, the phosphor sheets 2 must be flexible. However, from the viewpoints of durability of the stimulable phosphor and formation of radiation images of high quality, it is desirable to avoid bending of the phosphor sheets. FIG. 2 to 4B show the second to fourth embodiments in which the phosphor sheets are fixed on rigid supporting materials formed to circulate the phosphor sheets without bending them.

Figure 2:
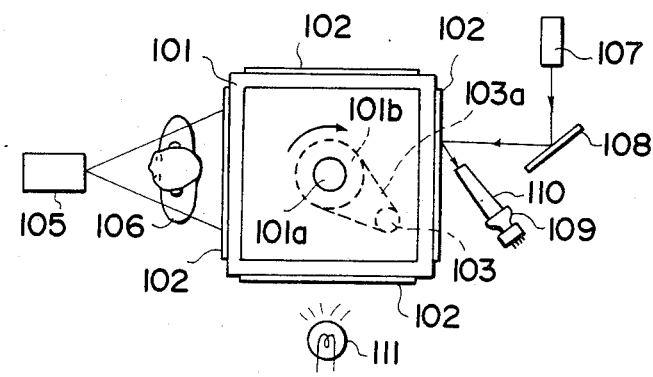
FIG. 2 is a schematic view showing the second embodiment of the system in accordance with the present invention.

In FIG. 2, four stimulable phosphor sheets 102 are fixed on the sides of a quadrangular prism-like turret 101. The turret 101 is provided with a shaft 101a on which a rotation member 101b such as a sprocket wheel is fixed. The rotation member 101b receives the driving force of a drive unit 103 via a driving force transfer member 103a formed of a chain or the like. The turret 101 is rotated at 90° intervals in the direction of the arrow by the drive unit 103. A radiation source 105 is opposed to one side of the turret 101, and a stimulating ray source 107, a light deflector 108, a photodetector 109 and a light transfer means 110 are positioned in the vicinity of the side opposite to the aforesaid side. An erasing light source 111 is positioned to face the side of the turret 101 adjacent to the aforesaid side facing the radiation source 105 on the side upstream of turret rotation from the aforesaid side. The radiation source 105, the stimulating ray source 107 and the other parts positioned around the turret 101 may be of the same types as those used in the first embodiment shown in FIG. 1, and the means for supporting and circulating the phosphor sheets employed in the system shown in FIG. 2 differs from that in FIG. 1. In the same way as in FIG. 1, when the turret 101 is stopped, the radiation source 105 is turned on to have the phosphor sheet 102 store a radiation transmission image of an object 106. After the turret 101 is rotated 90° twice, the phosphor sheet 102 carrying the radiation image stored thereon is stopped at the position facing the light deflector 108, the photodetector 109 and the like, and scanned with the stimulating ray emitted from the stimulating ray source 107 to have the phosphor sheet 102 emit light upon stimulation thereof. The light emitted from the phosphor sheet 102 is photoelectrically read out by the photodetector 109, which outputs an electric image signal corresponding to the radiation image. In the system shown in FIG. 2, since it is difficult to conduct the subsidiary scanning of the stimulating ray by the rotation of the turret 101, the other subsidiary scanning methods described above are employed. After the radiation image is read out from the phosphor sheet 102, the turret 101 is rotated 90° to position the phosphor sheet 102 at the erasing light source 111, where the radiation energy remaining on the phosphor sheet 102 is erased for reusing the sheet.

In FIG. 2, the phosphor sheet 102 is free of any process at one of the four stages of the turret 101. The process-free stage is not limited to the position shown in FIG. 2. Accordingly, it is also possible to form the system in which three phosphor sheets are fixed on a triangular prism-like turret. When it takes a long time to conduct the erasing step, two erasing stages may be installed.

Figure 3:
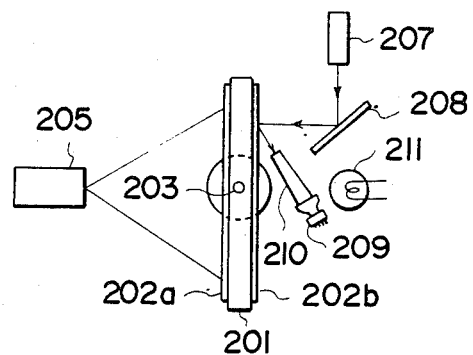
FIG. 3 is a schematic view showing the third embodiment of the system in accordance with the present invention.

In the present invention, any number of stimulable phosphor sheets may be fixed on the supporting material, and the erasing zone need not be positioned independently from the zone for conducting the image recording or the image read-out. For example, in the third embodiment shown in FIG. 3, a plate-like supporting material 201 rotatable at 180° intervals around a drive shaft 203 is used, and two phosphor sheets 202a and 202b are mounted on both sides of the supporting material 201. A radiation source 205 is opposed to the phosphor sheet 202a, while a stimulating ray source 207, a light deflector 208, a photodetector 209, a light transfer means 210, and an erasing light source 211 are opposed to the phosphor sheet 202b. The supporting material 201 is rotated at 180° intervals via the drive shaft 203, and the image recording and the image read-out are repeated for the phosphor sheets 202a and 202b. The erasing light source 211 is turned off when the image read-out is conducted, and is turned on after the image read-out is finished. After the erasing light source 211 is turned off, the supporting material 201 is rotated to move the phosphor sheets 202a and 202b. When the plate-like supporting material 201 is used, it is of course possible to fix the phosphor sheet on only one side of thereof. In this case, however, the image recording and read-out speed drops since the image recording and the image read-out cannot be conducted simultaneously. In the embodiments of FIGS. 2 and 3, a means for cleaning the phosphor sheets, such as the cleaning roller 12 shown in FIG. 1, is not installed. However, if necessary, it is possible to use a self-traveling type cleaning roller which moves to clean the surfaces of the phosphor sheets after the erasing step.

Figure 4A:
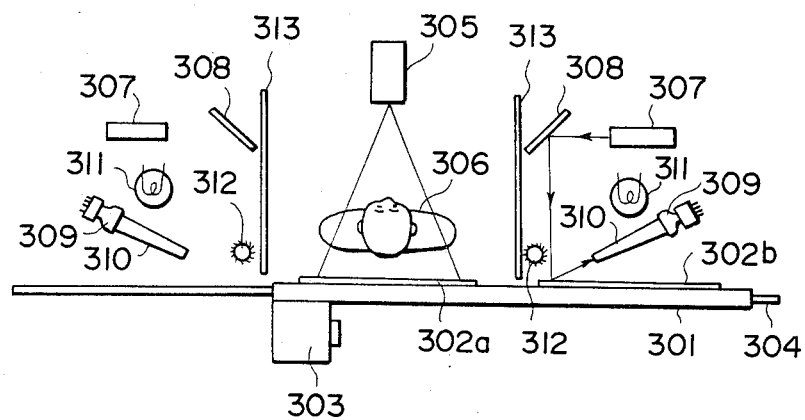
FIGS. 4A and 4B are schematic diagrams showing the fourth embodiment of the system in accordance with the present invention.
Figure 4B:
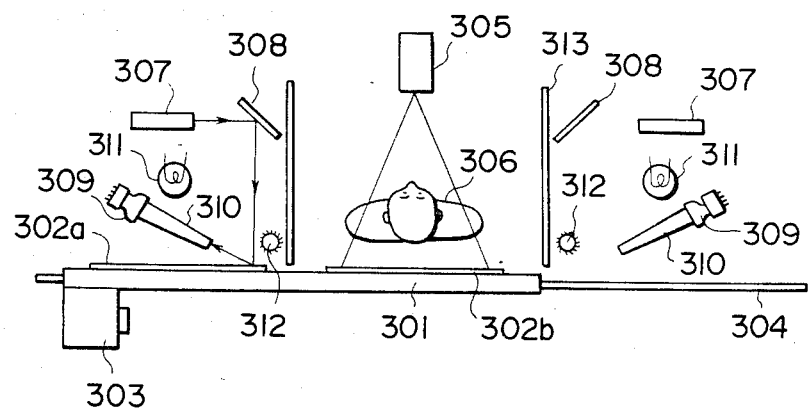

Instead of rotating the phosphor sheet supporting material as described above, it may be moved in any other ways, for example, may be linearly reciprocated. In the fourth embodiment shown in FIGS. 4A and 4B, a plate-like supporting material 301 is placed on a rail 304 for reciprocation therealong by use of a drive unit 303 for driving, for example, a pinion gear which is engaged with a rack on the side of the rail 304 to form a rack-pinion mechanism. Two phosphor sheets 302a and 302b are fixed on the supporting material 301. A radiation source 305 is positioned on the side facing the center of the rail 304, where the phosphor sheet 302a is positioned in the diagram. The image read-out sections comprising a stimulating ray source 307, a light deflector 308, a photodetector 309 and a light transfer means 310 are positioned on both sides of the radiation source 305. Each image read-out section is also provided with an erasing light source 311, and isolated from the radiation source 305 by a light shielding plate 313. Cleaning rollers 312 are positioned in the exteriors of and near to the light shielding plates 313. The supporting material 301 is reciprocated on the rail 304 by the drive unit 303, and alternately positioned as shown in FIGS. 4A and 4B. When the supporting material 301 is set in the position shown in FIG. 4A, a radiation image is recorded on the left phosphor sheet 302a, and the image read-out is conducted for the right phosphor sheet 302b. The subsidiary scanning in the image read-out step may be effected by moving the stimulating ray source and read-out apparatus or by moving the supporting material 301, as described above. After the image read-out is finished, the erasing light source 311 is turned on for a predetermined length of time to erase the residual radiation energy on the phosphor sheet 302b. At this time, since the light emitted from the erasing light source 311 is shielded by the light shielding plate 313, the radiation image stored on the phosphor sheet 302a is not adversely affected by the erasing light. After the erasing step for the phosphor sheet 302b is finished, the supporting material 301 is moved to left. At this time, the cleaning roller 312 is moved from the retracting position shown in the diagram to the position contacting the phosphor sheet 302b, and clean the surface of the phosphor sheet 302b being moved to left. After the phosphor sheet 302b has passed through the cleaning roller 312, the cleaning roller 312 is returned to the retracting position. After the supporting material 301 is moved to the position shown in FIG. 4B, the radiation image stored on the left phosphor sheet 302a in the condition shown in FIG. 4A is read out, and the image recording is conducted for the erased and cleaned right phosphor sheet 302b. Thereafter, the supporting material 301 is returned to the position shown in FIG. 4A, while the erasing and cleaning is effected for the left phosphor sheet 302a to make it reusable. When it is not necessary to increase the speed of this system, only one phosphor sheet may be used, and the image recording and the image read-out may be conducted alternately.

In order to obtain a radiation image having an excellent diagnostic efficiency and accuracy, it is preferable to investigate the recording condition or the recording pattern of the radiation image stored on the stimulable phosphor sheets before conducting the read-out, and set the read-out gain of the photoelectric read-out means, the scale factor, and the signal processing conditions based on the recording condition or pattern. For this purpose, it is proposed to read out the pattern of the radiation image in advance by use of a stimulating ray of low energy (this operation is referred to as the preliminary read-out), and then to determine the read-out condition and conduct the read-out for obtaining a radiation image for use in diagnosis (this operation is referred to as the final read-out), as disclosed in Japanese Patent Application Nos. 56(1981)-165111, 56(1981)-165112, 56(1981)-165113, 56(1981)-165114 and 56(1981)-165115. In the present invention, the preliminary read-out may be conducted by installing the preliminary read-out section on the side upstream from the aforesaid image read-out section, or by using the aforesaid image read-out section both for preliminary read-out and for final read-out.

In the embodiments of FIGS. 1 to 4A, at least one phosphor sheet is fixed on the supporting material. However, it is also possible to use an endless supporting material provided with a stimulable phosphor layer directly formed thereon. For example, the phosphor layer may be formed on the surface of an endless belt or a rotatable drum. The fifth to seventh embodiments of the system having such a configuration are described below with reference to FIGS. 5 to 8.

Figure 5:
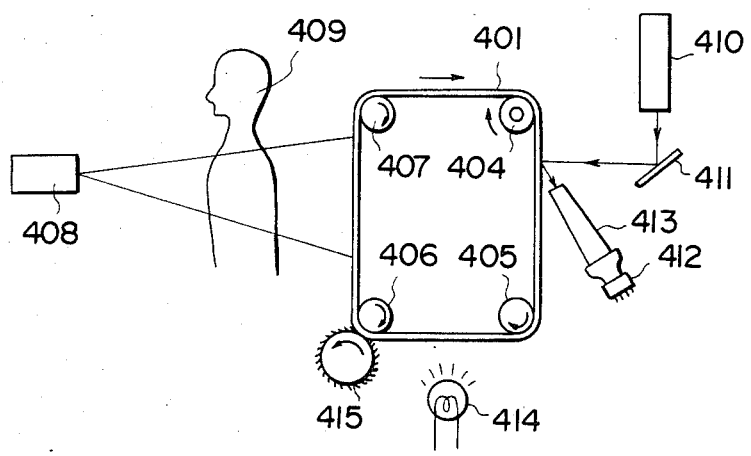
FIG. 5 is a schematic view showing the fifth embodiment of the system in accordance with the present invention.
Figure 6:
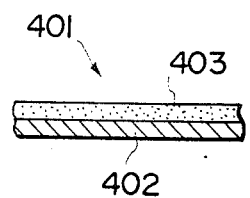
FIG. 6 is an enlarged view showing a part of the system shown in FIG. 5.

In FIG. 5, an endless belt-like recording member 401 is used. As shown in FIG. 6, the recording member 401 is provided with a stimulable phosphor layer 403 (recording material) formed on the surface of an endless belt-like supporting material 402. The recording member 401 is applied on a cylindrical driving roller 404 and cylindrical driven rollers 405, 406 and 407, and is moved in the direction of the arrow by the driving roller 404 which is rotated by a drive unit (not shown). A radiation source 408 is positioned on the side facing the portion of the recording member 401 between the driven rollers 406 and 407. The radiation source 408 may be an X-ray source or the like, and projects a radiation transmission image of an object 409 positioned between the radiation source 408 and the portion of the recording member 401 between the driven rollers 406 and 407 onto the recording member 401. A stimulating ray source 410 for emitting a stimulating ray such as a laser beam, a light deflector 411 formed of a galvanometer mirror or the like for deflecting the stimulating ray emitted from the stimulating ray source 410 in the width direction of the recording member 401, and a photodetector 412 for reading out the light emitted from the phosphor layer 403 upon stimulation thereof by the stimulating ray are opposed to the portion of the recording member 401 between the driving roller 404 and the driven roller 405. The photodetector 412 may be formed of a head-on type photomultiplier, a photoelectric amplification channel plate or the like, and photoelectrically detects the light emitted from the phosphor layer 403 upon stimulation thereof and guided by a light transfer means 413. An erasing light source 414 is positioned to face the portion of the recording member 401 between the driven rollers 405 and 406. The erasing light source 414 emits light having a wavelength within the stimulation wavelength range of the phosphor layer 403 onto the phosphor layer 403 to cause it to emit the radiation energy stored thereon. The erasing light source 414 may be formed, e.g., of a tungsten-filament lamp, halogen lamp, infrared lamp, or laser source as described in Japanese Unexamined Patent Publication No. 56(1981)-11392. Since the radiation energy stored on the phosphor layer 403 can also be eliminated by heating it as disclosed, for example, in Japanese Unexamined Patent Publication No. 56(1981)-12599, the erasing light source 414 may be replaced by a heating means. A cylindrical cleaning roller 415 is opposed to the driven roller 406 with the recording member 401 intervening therebetween. The cleaning roller 415 is rotated counterclockwise in the diagram by a drive unit (not shown), and removes dust from the surface of the recording member 401 moving in contact with the cleaning roller 415. If necessary, the cleaning roller 415 may be of an electrostatic attraction type.

The light transfer means 413 may be of the same type as the light transfer means 10 shown in FIG. 1.

The radiation image recording and read-out system shown in FIG. 5 is operated as described below. The recording member 401 is intermittently moved the distance corresponding to one-fourth of the entire circumference thereof at a time by the driving roller 404. When the recording member 401 is stopped, the radiation source 408 is turned on to cause the phosphor layer 403 of the recording member 401 between the driven rollers 406 and 407 to store the radiation transmission image of the object 409. After the recording member 401 is moved twice the distance of one-fourth its circumference each time, the portion of the phosphor layer 403 carrying the radiation image stored thereon is positioned between the driving roller 404 and the driven roller 405, and scanned with the stimulating ray emitted from the stimulating ray source 410. Scanning is conducted in the width direction of the recording member 401 (main scanning) by the light deflector 411, and also in the length direction of the recording member 401 (subsidiary scanning) by the movement of a stage (not shown) carrying the stimulating ray source 410, the light deflector 411, the photodetector 412 and the light transfer means 413 in the length direction of the recording member 401. The stage can be easily formed by use of a known linear movement mechanism. Upon exposure to the stimulating ray, the phosphor layer 403 emits light in the pattern of the radiation image stored thereon. The emitted light is inputted to the photodetector 412 via the light transfer means 413, and an electric signal corresponding to the radiation image stored on the phosphor layer 403 is outputted from the photodetector 412. After the radiation image is read out in this way, the recording member 401 is further moved the distance of one-fourth the circumference thereof and stopped. In this condition, the portion of the phosphor layer 403 from which the radiation image has been read out is positioned between the driven rollers 405 and 406, and exposed to the erasing light emitted from the erasing light source 414 to eliminate the radiation energy of the radiation image remaining on the phosphor layer 403 after the read-out step, the radiation emitted from radioactive isotopes such as $^{266}$Ra and $^{40}$K existing in trace amounts in the stimulable phosphor, and environmental radiations stored in the stimulable phosphor. In this way, the phosphor layer 403 is recovered to the condition usable for recording a further radiation image. Thereafter, the recording member 401 is moved until the erased portion of the phosphor layer 403 is positioned between the driven rollers 406 and 407. Midway during this movement, dust on the surface of the recording member 401 is removed by the cleaning roller 415. The recording member 401 free from any radiation energy and dust is reused to record a radiation image at the radiation source 408.

As described above, the recording member 401 is circulated and reused through the erasing step conducted by the erasing light source 414 and the cleaning step effected by the cleaning roller 415. A portion of the recording member 401 passes through the image recording, image read-out and image erasing steps while the recording member 401 rotates one turn. It is, of course, possible to simultaneously conduct these three steps for the three different portions of the recording member 401, respectively, when the recording member 401 is stopped. In this case, it is possible to improve the image processing speed.

In the embodiment shown in FIG. 5, since the phosphor layer 403 is fixed on the endless belt-like supporting material 402 and reused through the circulation of the supporting material 402, there is no risk of the stimulable phosphor being damaged unlike the method in which discrete phosphor sheets are conveyed one by one. Further, since the mechanism for circulating the phosphor can be formed only of a simple endless belt drive mechanism, the system is easy to design and manufacture. Also, since a single recording member 401 is circulated and reused, the quality of the reproduced images does not fluctuate.

In the same way as in the first embodiment, the electric image signal obtained from the photodetector 412 may immediately be sent to a reproducing apparatus to reproduce the radiation image as a hard copy or display it on a CRT, or may be digitized and temporarily stored on a high-density recording medium such as a magnetic tape, magnetic disk or optical disk to later reproduce the radiation image therefrom.

In the fifth embodiment shown in FIG. 5, the subsidiary scanning for reading out the radiation image is conducted by moving the stimulating ray source and read-out apparatus with respect to the recording member 401 when it is being halted. However, it is also possible to maintain the stimulating ray source and read-out apparatus stationary, and move the recording member 401 to conduct the subsidiary scanning. For this purpose, the recording member 401 may be moved at the subsidiary scanning speed after the image recording is over, and the read-out may be carried out during this movement of the recording member 401. It is also possible to conduct the image recording by use of the slit exposure method while the recording member 401 is being moved, thereby to effect the image recording and the image read-out without stopping the recording member 401.

Figure 7:
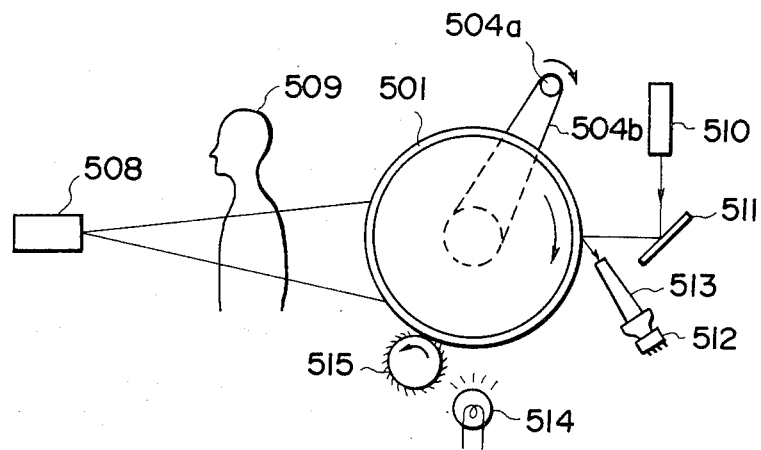
FIG. 7 is a schematic view showing the sixth embodiment of the system in accordance with the present invention.
Figure 8:
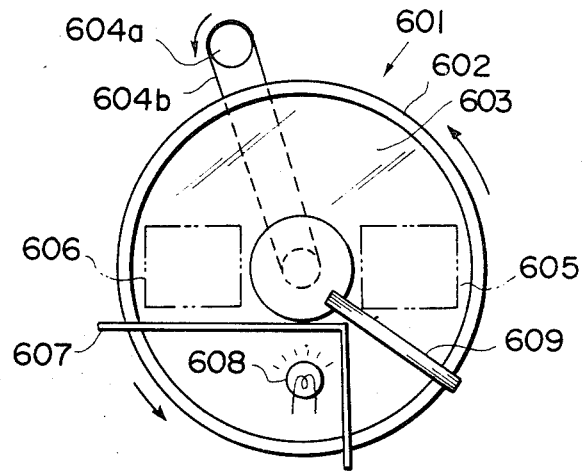
FIG. 8 is a schematic view showing the seventh embodiment of the system in accordance with the present invention.

In the fifth embodiment shown in FIG. 5, an endless belt-like recording member 401 which is flexible and can be bent freely is used. However, from the viewpoint of durability of the recording material and formation of fine radiation images, it is desirable that the recording material be rigid and is not bent during its use. FIGS. 7 and 8 show the sixth and seventh embodiments in which a rigid recording material is used.

In FIG. 7, a recording member 501 is formed of a stimulable phosphor provided on the peripheral surface of a drum-like supporting material. To the recording member 501 is transferred the driving force of a driving shaft 504a of a drive unit (not shown) via a chain 504b, and the recording member 501 is intermittently rotated in the direction of the arrow. Around the drum-like recording member 501 are positioned a radiation source 508, a stimulating ray source 510, a light deflector 511, a photodetector 512, a light transfer means 513, an erasing light source 514, and a cleaning roller 515, which are of the same types as those employed in FIG. 5. The system shown in FIG. 7 is similar to that shown in FIG. 5, except that the recording member 501 has a different shape and is driven in the different way. In the same way as in FIG. 5, the recording member 501 is exposed to a radiation passing through an object 509 to have a radiation image stored thereon, and scanned with a stimulating ray emitted from the stimulating ray source 510 to obtain an electric signal corresponding to the radiation image from the photodetector 512.

In FIG. 8, a recording member 601 is comprised of a stimulable phosphor layer 603 provided on the side of a disk-like supporting material 602. The recording member 601 is intermittently rotated one-fourth turn at a time in the direction of the arrow by a driving shaft 604a of a drive unit (not shown) via a chain 604b. Above the phosphor layer 603 is positioned an image recording zone 605, in which the phosphor layer 603 is exposed to a radiation passing through an object (not shown) to have a radiation image stored thereon. In the position 180° spaced apart from the image recording zone 605 is located an image read-out zone 606 provided with an image read-out apparatus (not shown) comprising a stimulating ray source, a scanning means such as a light deflector, a photodetector and a light transfer means of the type described above. Downstream from the image read-out zone 606 is positioned an erasing light source 608 surrounded by a light shielding member 607. A cleaning roller 609 is positioned downstream of the erasing light source 608 and upstream of the image recording zone 605. Also in the system shown in FIG. 8, the recording member 601 is circulated and reused while the erasing and cleaning are conducted by use of the erasing light source 608 and the cleaning roller 609. In this seventh embodiment, since the phosphor layer 603 is moved on a plane, the light shielding member 607 is employed to prevent the erasing light emitted from the erasing light source 608 from adversely affecting the image recording zone 605 and the image read-out zone 606. The light shielding member may also be employed in the embodiments shown in FIGS. 5 and 7, if necessary.

In the embodiments of FIGS. 7 and 8, since the recording material is formed rigidly and is not bent during operation, it exhibits higher durability, yields a finer visible image, and is easier to manufacture than an endless belt-like recording material.

In the embodiments shown in FIGS. 5, 7 and 8, the recording material is intermittently rotated one-fourth turn at a time. However, it is of course possible to rotate the recording material at different intervals. For example, in the system shown in FIG. 5, the recording material may be installed in a triangular form and intermittently rotated one-third turn each time. Further, it is not always necessary to position the erasing zone independently of the image recording zone or the image read-out zone. For example, the erasing light source may be positioned in the interior of the image read-out zone, and used in such a way that it is turned off during the image read-out operation and turned on after the image read-out is finished. In this case, it is possible to rotate the recording material a half turn at a time. Although it is not always necessary to clean the recording material by use of the cleaning roller, the cleaning is effective to improve the quality of the reproduced radiation image.

In the embodiments described above, a plurality of stimulable phosphor sheets or a plurality of portions of a phosphor layer are sequentially passed through the recording, read-out and erasing steps to sequentially conduct the recording, read-out and erasing for each phosphor sheet or each phosphor layer portion. However, it is also possible to first conduct the recording for all phosphor sheets or phosphor layer portions, and then collectively carry out the read-out for all radiation images stored thereon, followed by the collective erasing. The erasing may be conducted immediately after reading out each radiation image. This method is useful for continuous radiography, for example, angiography and kymography.

For this purpose, in FIG. 1, the phosphor sheets 2 may be positioned on the endless belt 1 over the entire circumference thereof in closely and equally spaced relation, and the recording may first be conducted for all phosphor sheets 2 by rotating the endless belt 1 one turn (at this time, the read-out and erasing apparatus are turned off). In this case, the read-out and the erasing may be conducted during the next rotation of the endless belt 1. Or, in FIG. 5, a stacker section may be formed to temporarily store a part of the endless belt-like recording member 401 in the zigzag form after a plurality of radiation images are recorded thereon, and thereafter to send this part to the read-out section to collectively read out the radiation images stored on that part. In FIG. 5, it is of course possible to collectively conduct the recording, read-out and/or erasing as described above with reference to FIG. 1. Conversely, the aforesaid stacker section may be formed in the system shown in FIG. 1. It should be understood that the aforesaid method in which the recording is collectively conducted, followed by collective read-out/erasing (or collective read-out and collective erasing), can be employed in any of the first to seventh embodiments described above.

Figure 9:
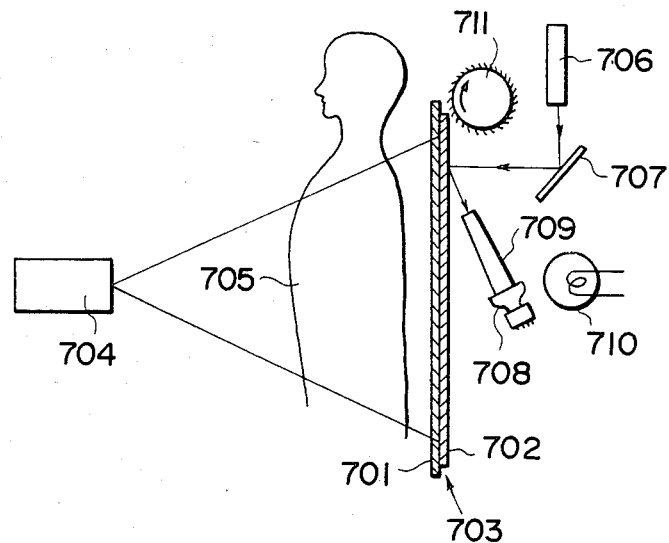
FIG. 9 is a schematic view showing the eighth embodiment of the system in accordance with the present invention.
Figure 10:
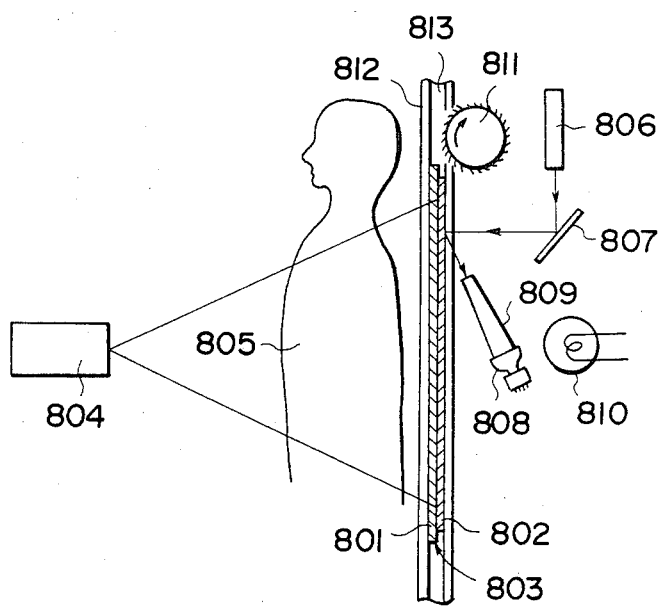
FIG. 10 is a schematic view showing the ninth embodiment of the system in accordance with the present invention.

In the present invention, it is also possible to use one recording material fixed on a plate-like supporting material, and repeat the image recording, read-out, and erasing steps for the recording material, as shown in FIGS. 9 and 10.

In FIG. 9 showing the eighth embodiment of the system in accordance with the present invention, a recording member 703 provided with a stimulable phosphor layer 702 on the surface of a stationary supporting material 701, which is made of a plate-like radiation transmitting material, is used to record radiation images. A radiation source 704 is opposed to the supporting material 701 of the recording member 703. The radiation source 704 may be an X-ray source or the like, and projects a radiation transmission image of an object 705, which is positioned between the radiation source 704 and the recording member 703, onto the phosphor layer 702 through the supporting material 701 to have the radiation image stored on the phosphor layer 702. On the phosphor layer side of the recording member 703 are positioned a stimulating ray source 706 for emitting a stimulating ray such as a laser beam, a light deflector 707 formed of a galvanometer mirror or the like for deflecting the stimulating ray emitted from the stimulating ray source 706 in the width direction of the recording member 703, a photodetector 708 for reading out the light emitted from the phosphor layer 702 upon stimulation thereof by the stimulating ray, and a light transfer means 709 for guiding the light emitted from the phosphor layer 702, which are mounted on a common stage (not shown). The photodetector 708 may be formed of a head-on type photomultiplier, a photoelectric amplification channel plate or the like, and photoelectrically detects the light emitted from the phosphor layer 702 upon stimulation thereof and guided by the light transfer means 709.

The light transfer means 709 may be of the same type as those employed in the above-mentioned embodiments. An erasing light source 710 is opposed to the phosphor layer 702 of the recording member 703, and the aforesaid stage also supports a cylindrical cleaning roller 711 which is rotated in the direction of the arrow by a drive unit (not shown). The erasing light source 710 emits light having a wavelength within the stimulation wavelength range of the phosphor layer 702 onto the phosphor layer 702 to cause it to emit the radiation energy stored thereon. The erasing light source 710 may be formed, e.g., of a tungsten-filament lamp, halogen lamp, infrared lamp, or laser source as described in Japanese Unexamined Patent Publication No. 56(1981)-11392. Since the radiation energy stored on the phosphor layer 702 can also be eliminated by heating it as disclosed, for example, in Japanese Unexamined Patent Publication No. 56(1981)-12599, the erasing light source 710 may be replaced by a heating means. The cleaning roller 711 rotates and moves in contact with the recording member 703 to remove dust from the surface of the phosphor layer 702. If necessary, the cleaning roller 711 may be of an electrostatic attraction type.

The system shown in FIG. 9 is operated as described below. After the object 705 is positioned between the recording member 703 and the radiation source 704, the radiation source 704 is turned on to cause the phosphor layer 702 to store the radiation transmission image of the object 705. After the recording of the radiation image is over, the stimulating ray source 706 is turned on to scan the phosphor layer 702 with the stimulating ray. Scanning is conducted in the width direction of the recording member 703 (main scanning) by the light deflector 707, and also in the vertical direction of the recording member 703 (subsidiary scanning) by the downward movement of the stage carrying the stimulating ray source 706, the light deflector 707, the photodetector 708, the light transfer means 709 and the cleaning roller 711. The stage can be easily formed by use of a known linear movement mechanism. Upon exposure to the stimulating ray, the phosphor layer 702 emits light in the pattern of the radiation image stored thereon. The emitted light is inputted to the photodetector 708 via the light transfer means 709, and an electric signal corresponding to the radiation image stored on the phosphor layer 702 is obtained from the photodetector 708. When the stage is moved down to conduct the subsidiary scanning, the cleaning roller 711 mounted on the stage is rotated to clean the surface of the phosphor layer 702. When the image read-out is finished and the whole surface of the phosphor layer 702 has been cleaned, the stage is returned to the waiting position above the recording member 703. Thereafter, the erasing light source 710 is turned on for a predetermined length of time, and the phosphor layer 702 is exposed to the erasing light emitted therefrom to eliminate the radiation energy of the radiation image remaining on the phosphor layer 702 after the read-out step, the radiation emitted from radioactive isotopes such as $^{266}$Ra and $^{40}$K existing in trace amounts in the stimulable phosphor, and environmental radiations stored in the stimulable phosphor. In this way, the phosphor layer 702 is recovered to the condition usable for recording a further radiation image. The recording member 703 which is now free from any radiation energy and dust is reused to record a radiation image.

In the embodiment shown in FIG. 9, since the stimulable phosphor is not moved, the mechanism is very simple, and the system can be easily designed and manufactured. Further, since one recording material is used repeatedly, the sheet control is easy and uniform visible images can be obtained.

FIG. 10 shows the ninth embodiment of the system in accordance with the present invention, in which the subsidiary scanning for reading out the radiation image is conducted by moving the recording material with respect to the stimulating ray source and image read-out apparatus fixed in the image read-out zone. Like the system shown in FIG. 9, the system shown in FIG. 10 employs a recording member 803 comprising a stimulable phosphor layer 802 formed on a supporting material 801 made of a radiation transmitting material, and is provided with a radiation source 804, a stimulating ray source 806, a light deflector 807, a photodetector 808, a light transfer means 809, an erasing light source 810, and a cleaning roller 811, which are of the same types as those employed in FIG. 9. However, unlike the embodiment shown in FIG. 9, the stimulating ray source 806, the light deflector 807, the photodetector 808, and the light transfer means 809 are fixed and do not move. The edges of the recording member 803 are fitted to the central grooves 813 of two vertically extending rails 812, and the recording member 803 can be vertically moved along the rails 812 by use of a linear movement mechanism (not shown) such as a rack-pinion mechanism. After the recording member 803 is exposed to a radiation coming from the radiation source 804 through an object 805 to have a radiation image stored thereon, the recording member 803 is scanned with the stimulating ray to read out the radiation image. At this time, the main scanning is conducted by use of the light deflector 807 in the same way as in FIG. 9, and the subsidiary scanning is effected by moving up the recording member 803 by use of the linear movement mechanism. As the recording member 803 is moved, the rotating cleaning roller 811 contacts it to remove dust therefrom. After the image read-out is finished and the recording member 803 is returned downward, the erasing light source 810 is turned on to erase the residual radiation image on the recording member 803.

In the embodiment of FIG. 10, the stimulable phosphor is moved to conduct the subsidiary scanning by moving the plate-like supporting material. The movement mechanism of this type can be formed more easily than a mechanism for conveying the sheet-like phosphors one by one.

In the embodiments shown in FIGS. 9 and 10, the stimulable phosphor is provided on the supporting material made of a radiation transmitting material and positioned on the side of the supporting material opposite to the radiation source. However, this configuration may be changed as desired. For example, the stimulable phosphor may be formed on a supporting material made of a material which cannot transmit a radiation, and may be positioned on the side facing the radiation source. In this case, it is possible to form the system so that, after the object moves away from the recording material, the stimulating ray source and the read-out apparatus are moved to the vicinity of the recording material. In case the supporting material is pervious to the stimulating ray and the light emitted from the stimulable phosphor upon stimulation thereof, it is possible to position the radiation source on the side facing the stimulable phosphor, and position the read-out apparatus on the side facing the supporting material.

In the embodiments of FIGS. 9 and 10, since only one recording material is used repeatedly, it can be easily replaced with a new one when the quality of the visible image reproduced therefrom drops. Thus, these embodiments greatly facilitate the quality control of the recording material. In these embodiments, after the movement of the phosphor relative to the image read-out section conducted for the subsidiary scanning is finished for one radiation image, the phosphor and the image read-out section are returned to the original position with respect to each other, and the subsidiary scanning movement is repeated. The movement for returning them to the original position corresponds to the movement of phosphor sheets for passing through the read-out section one after another in the above-mentioned embodiments in which many phosphor sheets are formed on the supporting material.

I claim:

1. A radiation image recording and read-out system comprising:
   (a) a supporting material,
   (b) at least one recording material fixed on said supporting material and comprised of a stimulable phosphor layer capable of storing a radiation image,
   (c) an image recording section for exposing said recording material to a radiation passing through an object to have a radiation transmission image of the object stored on said recording material,
   (d) an image read-out section provided with a stimulating ray source for emitting a stimulating ray for scanning said recording material carrying said radiation image stored thereon, and a photoelectric read-out means for obtaining an electric image signal by reading out light emitted from said recording material scanned and stimulated with the stimulating ray,
   (e) a means for circulating said recording material on said supporting material with respect to said image read-out section for enabling reuse of said recording material by repeatedly moving said supporting material and said image read-out section with respect to each other, and
   (f) an erasing means for eliminating the radiation energy remaining on said recording material prior to image recording on said recording material after the radiation image is read out therefrom at said image read-out section.

2. A system as defined in claim 1 wherein said supporting material is an endless supporting material.

3. A system as defined in claim 2 wherein said endless supporting material is an endless belt.

4. A system as defined in claim 2 wherein said endless supporting material is a rotatable drum.

5. A system as defined in any of claims 1 to 4 wherein said recording material is a stimulable phosphor layer formed on said supporting material.

6. A system as defined in any of claims 1 to 4 wherein said recording material is a stimulable phosphor sheet releasably secured to said supporting material.

7. A system as defined in any of claims 1 to 4 wherein said supporting material is capable of being circulated between said image recording section and said image read-out section.

8. A system as defined in claim 1 wherein said supporting material is a plate-like supporting material.

9. A system as defined in claim 8 wherein said plate-like supporting material is stationary and is made of a radiation transmitting material, and the system is formed in such a way that said image recording section conducts image recording on said recording material from one side of said supporting material, and image read-out section conducts image read-out from the other side of said supporting material.

10. A system as defined in claim 8 wherein said plate-like supporting material is capable of being moved with respect to said image read-out section for conducting scanning with the stimulating ray.

* * * * *